United States Patent

Fest et al.

[11] Patent Number: 4,990,637
[45] Date of Patent: Feb. 5, 1991

[54] 1-BENZYLSULPHONYL-3-HETEROARYL-(THIO)UREA HERBICIDES

[75] Inventors: Christa Fest, Wuppertal; Klaus-Helmut Müller, Duesseldorf; Theodor Pfister, Monheim; Hans-Jochem Riebel, Wuppertal; Ernst Kysela, Bergisch-Gladbach; Hans-Joachim Santel, Leverkusen; Robert R. Schmidt, Bergisch-Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 472,520

[22] Filed: Jan. 30, 1990

Related U.S. Application Data

[62] Division of Ser. No. 268,419, Nov. 8, 1988, Pat. No. 4,927,454, which is a division of Ser. No. 130,772, Dec. 9, 1987, Pat. No. 4,806,147.

[30] Foreign Application Priority Data

Dec. 16, 1986 [DE]  Fed. Rep. of Germany ....... 3642824

[51] Int. Cl.$^5$ ............................................. C07C 303/00
[52] U.S. Cl. ....................................... 562/41; 562/870; 562/828; 564/90
[58] Field of Search ............. 558/61, 19; 568/630, 568/655; 564/91, 90; 562/870, 41, 828

[56] References Cited

U.S. PATENT DOCUMENTS 4,476,056  10/1984  Pawson ............................ 568/437

FOREIGN PATENT DOCUMENTS 0068591  1/1983  European Pat. Off. ............ 568/630
0096002  12/1983  European Pat. Off. ............ 568/630
2704928  8/1977  Fed. Rep. of Germany ........ 558/61
3228101  2/1984  Fed. Rep. of Germany ........ 558/61

1596922  6/1970  France ................................. 558/61

Primary Examiner—Mary C. Lee
Assistant Examiner—Robert C. Whittenbaugh
Attorney, Agent, or Firm—Sprung Horn Kramer & Woods

[57] ABSTRACT

Herbicidally active novel substituted 1-benzylsulphonyl-3-heteroaryl(thio)-ureas of the formula

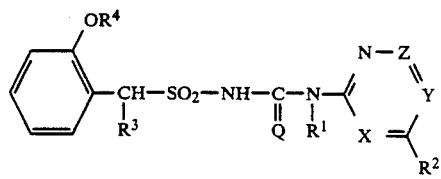

in which
$Q_1$ represents oxygen or sulphur,
$R^1$ represents hydrogen, or represents optionally substituted radicals from the series comprising alkyl, alkenyl, alkynyl and aralkyl,
$R^2$ represents hydrogen, halogen, hydroxyl, alkyl, halogenoalkyl, alkoxy, halogenoalkoxy, alkylthio, halogenoalkylthio, amino, alkylamino or dialkylamino,
$R^3$ represents hydrogen or alkyl,
$R^4$ represents halogenoalkyl,
X represents nitrogen or a —CH grouping,
Y represents nitrogen or a —CR$^5$ grouping,
$R^5$ represents hydrogen, halogen, cyano, alkyl, formyl, alkyl-carbonyl or alkoxy-carbonyl,
Z represents nitrogen or a —CR$^6$ grouping, and
$R^6$ represents hydrogen, halogen, hydroxyl, alkyl, halogenoalkyl, alkoxy, halogenoalkoxy, alkylthio, alkylamino or dialkylamino, and salts thereof with metals and basic organic nitrogen compounds. The benzylsulphonyl moieties are also new.

7 Claims, No Drawings

1-BENZYLSULPHONYL-3-HETEROARYL-(THI-O)UREA HERBICIDES

This is a division of application Ser. No. 268,419 filed Nov. 8, 1988, now U.S. Pat. No. 4,927,454 which is a division of application Ser. No. 130,772, filed Dec. 9, 1987, now U.S. Pat. No. 4,806,147.

The invention relates to new substituted 1-benzylsulphonyl-3-heteroaryl-(thio)ureas, a process and new intermediate products for their preparation and their use as herbicides.

It is known that certain 1-benzylsulphonyl-3-heteroaryl-(thio)ureas, such as, for example, 1-(2-methoxycarbonyl-benzylsulphonyl)-3-(4,6-dimethoxy-pyrimi-din-2-yl)-urea, have a herbicidal action. However, the action of these compounds is not always completely satisfactory (compare U.S. Patent Specification No. 4,420,325).

New substituted 1-benzylsulphonyl-3-heteroaryl-(thi-o)ureas of the general formula (I)

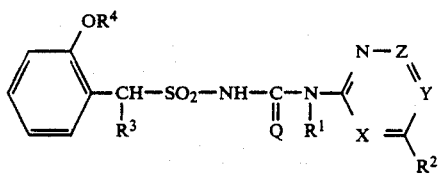

in which
Q represents oxygen or sulphur,
$R^1$ represents hydrogen, or represents optionally substituted radicals from the series comprising alkyl, alkenyl, alkynyl and aralkyl,
$R^2$ represents hydrogen, halogen, hydroxyl, alkyl, halogenoalkyl, alkoxy, halogenoalkoxy, alkylthio, halogenoalkylthio, amino, alkylamino or dialkylamino,
$R^3$ represents hydrogen or alkyl,
$R^4$ represents halogenoalkyl,
X represents nitrogen or a —CH grouping,
Y represents nitrogen or a —$CR^5$ grouping,
wherein
$R^5$ represents hydrogen, halogen, cyano, alkyl, formyl, alkyl-carbonyl or alkoxy-carbonyl and
Z represents nitrogen or a —$CR^6$ grouping,
wherein
$R^6$ represents hydrogen, halogen, hydroxyl, alkyl, halogenoalkyl, alkoxy, halogenoalkoxy, alkylthio, alkylamino or dialkylamino, and salts of compounds of the formula (I) with metals and basic organic nitrogen compounds have now been found.

The new substituted 1-benzylsulphonyl-3-heteroaryl-(thio)ureas of the formula (I) are obtained by a process in which 2-halogenoalkoxy-benzylsulphonyl iso(thio)cyanates of the formula (II)

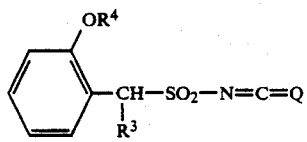

in which
Q, $R^3$ and $R^4$ have the abovementioned meanings, are reacted with heteroarylamines of the formula (III)

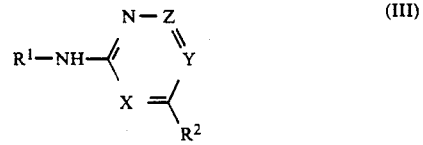

in which
$R^1$, $R^2$, X, Y and Z have the abovementioned meanings,
if appropriate in the presence of diluents and if appropriate in the presence of catalysts, and, if appropriate, the products thus obtained are converted into salts by customary methods.

The new substituted 1-benzylsulphonyl-3-heteroaryl-(thio)ureas of the formula (I) are distinguished by a powerful herbicidal activity.

Surprisingly, the new compounds of the formula (I) exhibit a considerably better herbicidal action than the already known 1-benzylsulphonyl-3-heteroaryl-(thio)ureas of the same type of action.

Other possible methods for the preparation of the compounds of the formula (I) according to the invention are given below, Q, $R^1$, $R^2$, $R^3$, $R^4$, X, Y and Z having the abovementioned meanings: (a) reaction of 2-halogenoalkoxy-benzylsulphonamides (IV) with N-heteroaryl-urethanes (V) ($R^7$: alkyl, benzyl or phenyl):

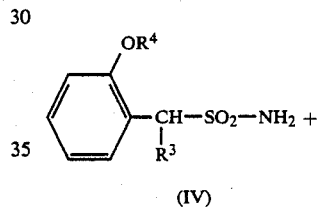

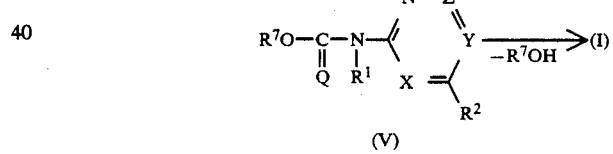

(b) reaction of N-(2-halogenoalkoxy-benzylsulphonyl)urethanes (VI) ($R^8$: alkyl, benzyl or phenyl) with heteroarylamines (III):

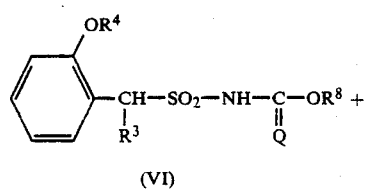

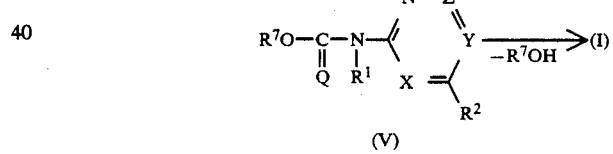

(c) reaction of 1-benzylsulphonyl-3-heteroaryl-(thi-o)ureas (VII) with "alkylating agents" (VIII) (W: nucleophilic leaving group):

$$\underset{(VII)}{\overset{OR^4}{\underset{R^3}{\text{Ph-CH-SO}_2\text{-NH-}\underset{Q}{\overset{\|}{C}}\text{-NH}}}\!\!\!-\!\!\!\overset{N-Z}{\underset{X}{\diagdown\!\!\diagup}}\!\!Y} \;+$$

$$\underset{(VIII)}{R^1-W} \xrightarrow[-HW]{} (I)$$

The invention preferably relates to compounds of the formula (I)
in which
Q represents oxygen or sulphur,
R¹ represent hydrogen, or represents $C_1$–$C_6$alkyl [which is optionally substituted by fluorine, cyano, $C_1$–$C_4$-alkoxy or $C_1$–$C_4$-alkylthio], or represents $C_3$–$C_6$-alkenyl or $C_3$–$C_6$-alkynyl [which are optionally substituted by fluorine or chlorine], or represents phenyl-$C_1$–$C_2$-alkyl [which is optionally substituted in the phenyl part by fluorine/ chlorine, nitro, cyano, methyl, methoxy or $C_1$–$C_2$-alkoxycarbonyl],
R² represents hydrogen, fluorine, chlorine, bromine, methyl, ethyl, trifluoromethyl, methoxy, ethoxy, difluoromethoxy, methylthio, ethylthio, amino, methylamino, ethylamino, dimethylamino or diethylamino,
R³ represents hydrogen or $C_1$–$C_4$-alkyl,
R⁴ represents halogeno-$C_1$–$C_4$-alkyl,
wherein
halogen represents fluorine and/or chlorine,
X represents nitrogen or a —CH grouping,
Y represents nitrogen or a —CR⁵ grouping,
wherein
R⁵ represents hydrogen, fluorine, chlorine, bromine, methyl, formyl, acetyl, methoxycarbonyl or ethoxycarbonyl and
Z represents nitrogen or a —CR⁶ grouping,
wherein
R⁶ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

The invention furthermore preferably relates to salts of compounds of the formula (I)—as defined above— with sodium, potassium, magnesium and calcium, and with monoalkyl-, dialkyl-, trialkyl-, benzyl-alkyl- and benzyl-dialkylamines with in each case up to 4 carbon atoms in the alkyl radicals, the alkyl radicals optionally in each case containing one substituent from the series comprising fluorine, chlorine, hydroxyl, methoxy, ethoxy and cyano.

The invention particularly relates to compounds of the formula (I)
in which
Q represents oxygen,
R¹ represents hydrogen or methyl,
R² represents hydrogen, chlorine, methyl, ethyl, trifluoromethyl, methoxy, ethoxy or difluoromethoxy,
R³ represents hydrogen,
R⁴ represents halogeno-$C_1$–$C_2$-alkyl,
wherein
halogen represents fluorine and/or chlorine,
X represents nitrogen or a —CH grouping,
Y represents nitrogen or a —CR⁵ grouping,
wherein
R⁵ represents hydrogen, fluorine, chlorine or methyl and
Z represents nitrogen or a —CR⁶ grouping,
wherein
R⁶ represents hydrogen, chlorine, methyl, ethyl, trifluoromethyl, methoxy, ethoxy or difluoromethoxy.

If, for example, 2-trifluoromethoxy-benzylsulphonyl isocyanate and 2-amino-4,6-dimethyl-pyrimidine are used as starting substances for the process according to the invention, the course of the reaction can be outlined by the following equation:

$$\underset{}{\text{Ph(OCF}_3\text{)-CH}_2\text{-SO}_2\text{-NCO}} + H_2N\text{-}\underset{CH_3}{\overset{CH_3}{\text{pyrimidine}}} \longrightarrow$$

$$\text{Ph(OCF}_3\text{)-CH}_2\text{-SO}_2\text{-NH-}\underset{O}{\overset{\|}{C}}\text{-NH-}\underset{CH_3}{\overset{CH_3}{\text{pyrimidine}}}$$

Formula (II) provides a definition of the 2-halogenoalkoxy-benzylsulphonyl iso(thio)cyanates to be used as starting substances in the process according to the invention. In this formula, Q, R³ and R⁴ preferably or particularly represent those radicals which have already been mentioned as preferred or as particularly preferred in connection with the description of the compounds of the formula (I) according to the invention.

Examples which may be mentioned of the starting substances of the formula (II) are: 2-difluoromethoxy-, 2-trifluoromethoxy-, 2-chlorodifluoromethoxy-, 2-dichloro-fluoromethoxy-, 2-(2-chloro-ethoxy-, 2-(2,2,2-trifluoro- ethoxy)-, 2-(1,1,2,2-tetrafluoro-ethoxy)- and 2-(2-chloro-1,1,2-trifluoro-ethoxy)-benzylsulphonyl isocyanate and -benzylsulphonyl isothiocyanate, and 2-difluoro-methoxy-, 2-trifluoromethoxy-, 2-chlorodifluoromethoxy-, 2-dichlorofluoromethoxy-, 2-(2-chloro-ethoxy)-, 2-(1,1,2,2-tetrafluoro-ethoxy)- and 2-(2-chloro-1,1,2-tri-fluoro-ethoxy)-α-methyl-benzylsulphonyl isocyanate and -α-methyl-benzylsulphonyl isothiocyanate.

The starting compounds of the formula (II) are not yet described in the literature. These compounds are obtained by a process in which
(a) in the case where Q represents oxygen, 2-halogeno-alkoxy-benzylsulphonamides of the formula (IV)

$$\underset{(IV)}{\overset{OR^4}{\underset{R^3}{\text{Ph-CH-SO}_2\text{-NH}_2}}}$$

in which

R[3] and R[4] have the abovementioned meanings, are reacted with about the equimolar amount of an alkyl isocyanate, such as, for example, butyl isocyanate, if appropriate in the presence of a catalyst, such as, for example, diazabicyclo-[2,2,2]-octane (DABCO), and in the presence of a diluent, such as, for example, xylene, at temperatures between 50° C. and 200° C., preferably between 80° C. and 150° C., and at least the equimolar amount of phosgene is at the same time passed in, or (b) in the case where Q represents sulphur, by a process in which 2-halogenoalkoxy-benzylsulphonamides of the above formula (IV) are reacted with carbon disulphide in the presence of an acid acceptor, such as, for example, potassium hydroxide, and if appropriate in the presence of a diluent, such as, for example, dimethylformamide, at temperatures between 0° C. and 50° C., and the product is then reacted with phosgene or thionyl chloride, if appropriate in the presence of a diluent, such as, for example, methylene chloride, at temperatures between 0° C. and 50° C. (compare Arch. Pharm. 299 (1966), 174).

Formula (IV) provides a definition of the 2-halogenoalkoxy-benzylsulphonamides to be used as intermediate products. In this formula, R[3] and R[4] preferably or particularly represent those radicals which have already been mentioned as preferred or as particularly preferred in connection with the description of the compounds of the formula (I) according to the invention.

Examples which may be mentioned of the intermediate products of the formula (IV) are: 2-difluoromethoxy-, 2-trifluoromethoxy-, 2-chlorodifluoromethoxy-, 2-dichlorofluoromethoxy-, 2-(2-chloro-ethoxy-, 2-(2,2,2-trifluoroethoxy)-, 2-(1,1,2,2-tetrafluoroethoxy)- and 2-(2-chloro-1,1,2-trifluoroethoxy)-benzylsulphonamide and the corresponding α-methyl-benzylsulphonamides The intermediate products of the formula (IV) are not yet described in the literature. These compounds are obtained by a process in which 2-halogenoalkoxy-benzylsulphonyl chlorides of the formula (IX)

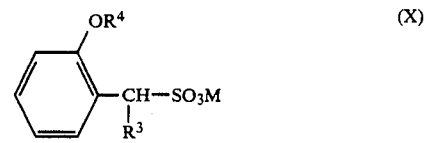

in which

R[3] and R[4] have the abovementioned meanings, are reacted with ammonia in at least the equimolar amount, if appropriate in the presence of a diluent, such as, for example, water, diethyl ether or tetrahydrofuran, at temperatures between −20° C. and +100° C., preferably between 0° C. and 80° C., and the product is worked up by customary methods.

Formula (IX) provides a definition of the 2-halogenoalkoxy-benzylsulphonyl chlorides to be used as intermediate products In this formula, R[3] and R[4] preferably or particularly represent those radicals which have already been mentioned as preferred or as particularly preferred in connection with the description of the compounds of the formula (I) according to the invention.

Examples which may be mentioned of the intermediate products of the formula (IX) are: 2-difluoromethoxy-, 2-trifluoromethoxy-, 2-chlorodifluoromethoxy-, 2-dichlorofluoromethoxy-, 2-(2-chloro-ethoxy)-, 2-(2,2,2-trifluoro-ethoxy)-, 2-(1,1,2,2-tetrafluoro-ethoxy)- and 2-(2-chloro-1,1,2-trifluoro-ethoxy)-benzylsulphonyl chloride and the corresponding α-methyl-benzylsulphonyl chlorides.

The intermediate products of the formula (IX) are not yet described in the literature. These compounds are obtained by a process in which 2-halogenoalkoxy-benzylsulphonic acids or salts thereof, of the formula (X)

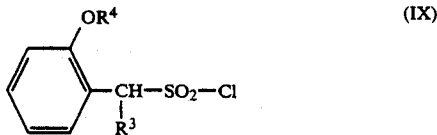

in which

M represents hydrogen or an alkali metal and

R[3] and R[4] have the abovementioned meanings, are reacted with at least the equimolar amount of a chlorinating agent, such as, for example, phosphorus pentachloride, phosphorus oxychloride or thionyl chloride, if appropriate in the presence of a diluent, such as, for example, methylene chloride, chloroform or carbon tetrachloride, at temperatures between 0° C. and 150° C., preferably between 20° C. and 100° C., and the mixture is worked up by customary methods.

Formula (X) provides a definition of the 2-halogenoalkoxy-benzylsulphonic acids and salts thereof to be used as intermediate products. In this formula, R[3] and R[4] preferably or particularly represent those radicals which have already been mentioned as preferred or as particularly preferred in connection with the description of the compounds of the formula (I) according to the invention, and M preferably and particularly represents hydrogen, sodium or potassium.

Examples which may be mentioned of the intermediate products of the formula (X) are: 2-difluoro- methoxy-, 2-trifluoromethoxy-, 2-chlorodifluoromethoxy-, 2-dichlorofluoromethoxy-, 2-(2-chloro-ethoxy)-, 2-(2,2,2-trifluoro-ethoxy)-, 2-(1,1,2,2-tetrafluoro-ethoxy)- and 2-(2-chloro-1,1,2-trifluoro-ethoxy)-benzylsulphonic acid and sodium and potassium salts thereof, and furthermore the corresponding α-methyl-benzylsulphonic acids and their sodium and potassium salts.

The intermediate products of the formula (X) are not yet described in the literature. These compounds are obtained by a process in which 2-halogenoalkoxy-benzyl chlorides of the formula (XI)

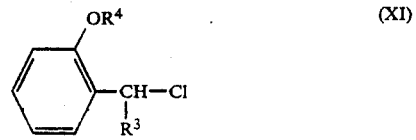

in which

R[3] and R[4] have the abovementioned meanings, are reacted with at least the equimolar amount of sodium thiosulphate or potassium thiosulphate in water at temperatures between 20° C. and 110° C. and the product is worked up by customary methods.

Formula (XI) provides a definition of the 2-halogenoalkoxy-benzyl chlorides to be used as intermediate products. In this formula, R[3] and R[4] preferably or particularly represent those radicals which have already been mentioned as preferred or as particularly preferred in connection with the description of the compounds of the formula (I) according to the invention.

Examples which may be mentioned of the intermediate products of the formula (XI) are: 2-difluoromethoxy-, 2-trifluoromethoxy-, 2-chlorodifluoromethoxy-, 2-dichlorofluoromethoxy-, 2-(2-chloro-ethoxy)-, 2-(1,1,2,2-tetrafluoro-ethoxy)- and 2-(2-chloro-1,1,2-tri-fluoro-ethoxy)-benzyl chloride and the corresponding α-methyl-benzyl chlorides.

The intermediate products of the formula (XI) are in some cases not yet described in the literature. For example, 2-trifluoromethoxy-benzyl chloride is as yet unknown. These compounds are obtained by a process in which 2-halogenoalkoxy-toluenes, for example 2-trifluoromethoxy-toluene, of the formula (XII)

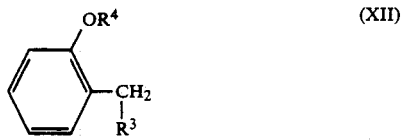
(XII)

in which

R³ and R⁴ have the abovementioned meanings, are reacted with not more than the equimolar amount of chlorine at temperatures between 50° C. and 180° C. under UV irradiation and the product is worked up by customary methods (compare, for example, DE-OS (German Published Specification) No. 2,150,955).

Formula (XII) provides a definition of the 2-halogenoalkoxy-toluenes to be used as intermediate products. In this formula, R³ and R⁴ preferably or particularly represent those radicals which have already been mentioned as preferred or as particularly preferred in connection with the description of the compounds of the formula (I) according to the invention.

Examples which may be mentioned of the compounds of the formula (XII) are: 2-difluoromethoxy-, 2-trifluoro-methoxy-, 2-chlorodifluoromethoxy-, 2-dichlorofluoromethoxy-, 2-(2-chloro-ethoxy)-, 2-(1,1,2,2-tetrafluoro-ethoxy)- and 2-(2-chloro-1,1,2-tri-fluoro-ethoxy)-toluene and the corresponding α-methyltoluenes.

The intermediate products of the formula (XII) are known and/or can be prepared by processes which are known per se (compare, for example, Tetrahedron Lett. 25 (1973), 2253-2256; and DE-OS (German Published Specification) No. 2,150,955).

Formula (III) provides a definition of the heteroarylamines furthermore to be used as starting substances in the preparation process according to the invention. In this formula, R¹, R², X, Y and Z preferably or particularly represent those radicals which have already been mentioned as preferred or as particularly preferred in connection with the description of the compounds of the formula (I) according to the invention. Examples of the starting substances of the formula (III) are given in Table 1 below.

TABLE 1-continued $$R^1-NH-\overset{N-Z}{\underset{X}{\overset{\|}{C}}}\overset{}{\underset{R^2}{\overset{Y}{\|}}} \quad (III)$$

| R¹ | N-Z, X, Y, R² structure | R¹ | N-Z, X, Y, R² structure |
|---|---|---|---|
| —CH₃ | pyrimidine with 4-C₂H₅, 2-CH₃ | —CH₃ | triazine with 4-CH₃, 6-CH₃, 2-CH₃ |
| —CH₃ | pyrimidine with 4-OC₂H₅, 6-OC₂H₅, 2-CH₃ | —CH₃ | pyrimidine with 4-CH₃, 6-Cl, 2-CH₃ |
| —CH₃ | triazine with OCH₃, CH₃, CH₃ | —CH₃ | triazine with OCH₃, OCH₃, CH₃ |
| —CH₃ | triazine with OC₂H₅, CH₃, CH₃ | —CH₃ | triazine with OC₂H₅, OC₂H₅, CH₃ |
| —CH₃ | triazine with OC₂H₅, OCH₃, CH₃ | —CH₃ | triazine with CH₃, SCH₃, CH₃ |
| —CH₃ | pyrimidine with OCHF₂, CH₃, CH₃ | —CH₃ | triazine with CH₃, N(CH₃)₂, CH₃ |
| —CH₃ | triazine with CH₃, SC₂H₅, CH₃ | —CH₃ | triazine with CH₃, N(C₂H₅)₂, CH₃ |

TABLE 1-continued $$R^1-NH-\overset{N-Z}{\underset{X}{\overset{\|}{C}}}\overset{Y}{\underset{R^2}{}}$$  (III)

| $R^1$ | ring | $R^1$ | ring |
|---|---|---|---|
| —CH₃ | 4-OCH₃, 6-SCH₃ triazine | —CH₃ | 4-OCH₃, 6-NHCH₃ triazine |
| —CH₃ | 4-OC₂H₅, 6-SCH₃ triazine | —CH₃ | 4-OCH₃, 6-NHC₂H₅ triazine |
| —CH₃ | 4-OCH₃, 6-SC₂H₅ triazine | —CH₃ | 4-OCH₃, 6-N(CH₃)₂ triazine |
| —CH₃ | 4-CF₃, 6-Cl pyrimidine | —CH₃ | 4-OCH₃, 6-Cl pyrimidine |
| —CH₃ | 4-OC₂H₅, 6-SC₂H₅ triazine | —CH₃ | 4-OCH₃, 6-N(C₂H₅)₂ triazine |
| —CH₃ | 4-CH₃, 6-NHCH₃ triazine | —CH₃ | 4-OC₂H₅, 6-NHCH₃ triazine |
| —CH₃ | 4-CH₃, 6-NHC₂H₅ triazine | —CH₃ | 4-OC₂H₅, 6-NHC₂H₅ triazine |

TABLE 1-continued $$R^1-NH-\overset{N-Z}{\underset{X}{\bigcirc}}\overset{Y}{\underset{R^2}{\bigcirc}} \quad \text{(III)}$$

| $R^1$ | ring | $R^1$ | ring |
|---|---|---|---|
| —CH₃ | triazine with OC₂H₅ and N(C₂H₅)₂ | —CH₃ | triazine with OC₂H₅ and N(CH₃)₂ |
| —CH₃ | triazine with SCH₃ and NHCH₃ | —CH₃ | triazine (N—N) with CH₃ and CH₃ |
| —CH₃ | triazine with SCH₃ and NHC₂H₅ | —CH₃ | pyridine with CH₃ and CH₃ |
| —CH₃ | triazine with SCH₃ and N(CH₃)₂ | —CH₃ | triazine with SCH₃ and N(C₂H₅)₂ |
| —CH₃ | triazine with SC₂H₅ and NHCH₃ | —CH₃ | triazine with SC₂H₅ and N(CH₃)₂ |
| —CH₃ | triazine with SC₂H₅ and N(C₂H₅)₂ | —CH₃ | triazine (N—N) with CH₃ and CH₃ |
| H | pyrimidine with CH₃ and CH₃ | H | pyrimidine with CH₃ |

TABLE 1-continued $$R^1-NH-\overset{N-Z}{\underset{X}{\overset{\|}{C}}}\overset{Y}{\underset{R^2}{\|}} \quad (III)$$

| R¹ | structure | R¹ | structure |
|---|---|---|---|
| H | 4-CH₃, 6-OCH₃-pyrimidin-2-yl | H | 4-C₂H₅-pyrimidin-2-yl |
| H | 4,6-di-OCH₃-pyrimidin-2-yl | H | 4-OCHF₂, 6-CH₃-pyrimidin-2-yl |
| H | 4,6-di-OC₂H₅-pyrimidin-2-yl | —CH₃ | 4-OC₂H₅, 6-Cl-pyrimidin-2-yl |
| H | 4,6-di-CH₃-1,3,5-triazin-2-yl | H | 4,6-di-OCH₃-1,3,5-triazin-2-yl |
| H | 4-OCH₃, 6-CH₃-1,3,5-triazin-2-yl | H | 4-OC₂H₅, 6-CH₃-1,3,5-triazin-2-yl |
| H | 4,6-di-OC₂H₅-1,3,5-triazin-2-yl | —CH₂C₆H₅ | 4-OC₂H₅, 6-OCH₃-1,3,5-triazin-2-yl |
| H | 4-CH₃, 6-SCH₃-1,3,5-triazin-2-yl | | |

TABLE 1-continued $$R^1-NH-\underset{X}{\overset{N-Z}{\underset{\|}{\bigg|}}}\overset{Y}{\underset{R^2}{\bigg|}} \quad (III)$$

| $R^1$ | structure | $R^1$ | structure |
|---|---|---|---|
| —C$_2$H$_5$ | 2-methyl-4,6-dimethylpyrimidine | —C$_2$H$_5$ | 4,6-dimethoxypyrimidine |
| —C$_2$H$_5$ | 2-methyl-4-methyl-6-methoxypyrimidine | —C$_2$H$_5$ | 2,4,6-trimethylpyrimidine (methyl at 2, methyl at 4, methyl at 6) |
| —C$_2$H$_5$ | 2-methyl-4,6-dimethoxypyrimidine | —C$_2$H$_5$ | 2-methyl-4-methylpyrimidine |
| —C$_2$H$_5$ | 2-methyl-4,6-diethoxypyrimidine | —CH$_3$ | 2-methyl-4-ethyl-6-chloropyrimidine |
| —CH$_3$ | 2-methyl-4-OCHF$_2$-6-CF$_3$-pyrimidine | —CH$_3$ | 2-methyl-4-OCHF$_2$-6-chloropyrimidine |
| —C$_2$H$_5$ | 2-methyl-4-ethylpyrimidine | —C$_2$H$_5$ | 2,6-dimethyl-triazine with CH$_3$ |
| —C$_2$H$_5$ | methoxy/methyl triazine | —C$_2$H$_5$ | dimethoxy triazine |

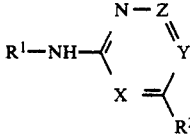

TABLE 1-continued
$$R^1-NH-\overset{N=Z}{\underset{X}{\rightleftarrows}}\overset{Y}{\underset{R^2}{}} \quad (III)$$
| R¹ | ![structure](N=Z/X/Y/R²) | R¹ | ![structure](N=Z/X/Y/R²) |
|---|---|---|---|
| —C₂H₅ | 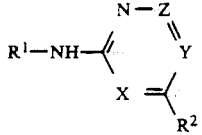 | —C₂H₅ | 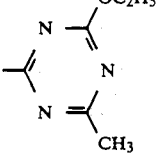 |
| —C₂H₅ | 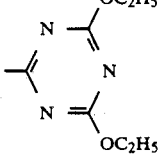 | —C₂H₅ | 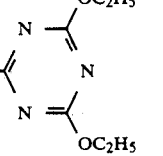 |
| —C₂H₅ | 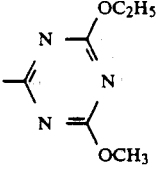 | —C₂H₅ | 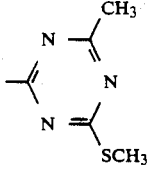 |
| —C₂H₅ | 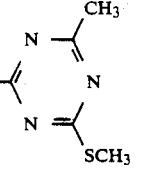 | —C₂H₅ | 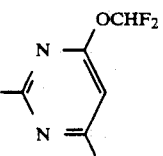 |
| —C₂H₅ | 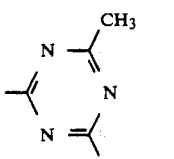 | —C₂H₅ | 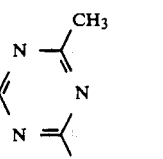 |
| —C₂H₅ | 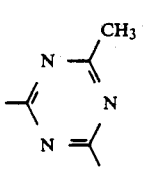 | —C₂H₅ | 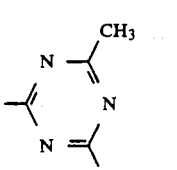 |
| —C₂H₅ | 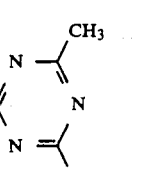 | —C₂H₅ | 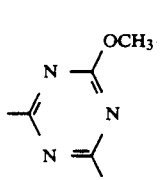 |

TABLE 1-continued

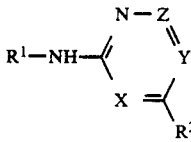
(III)

| R¹ | ![structure] | R¹ | ![structure] |
|---|---|---|---|
| —$C_2H_5$ | triazine with $OC_2H_5$ and $SC_2H_5$ | —$C_2H_5$ | triazine with $OCH_3$ and $N(C_2H_5)_2$ |
| —$C_2H_5$ | triazine with $CH_3$ and $NHCH_3$ | —$C_2H_5$ | triazine with $OC_2H_5$ and $NHCH_3$ |
| —$C_2H_5$ | triazine with $CH_3$ and $NHC_2H_5$ | —$C_2H_5$ | triazine with $OC_2H_5$ and $NHC_2H_5$ |
| —$C_2H_5$ | triazine with $OC_2H_5$ and $N(C_2H_5)_2$ | —$C_2H_5$ | triazine with $OC_2H_5$ and $N(CH_3)_2$ |
| —$C_2H_5$ | triazine with $SCH_3$ and $NHCH_3$ | —$C_2H_5$ | triazine with $CH_3$ (N—N) |
| —$C_2H_5$ | triazine with $SCH_3$ and $NHC_2H_5$ | —$C_2H_5$ | pyridine with $CH_3$, $CH_3$ |
| —$C_2H_5$ | triazine with $SCH_3$ and $N(CH_3)_2$ | —$C_2H_5$ | triazine with $SCH_3$ and $N(C_2H_5)_2$ |

TABLE 1-continued $$R^1-NH-\overset{N-Z}{\underset{X}{\Big|}}\overset{}{\underset{R^2}{\Big\|}}Y \quad \text{(III)}$$

| R¹ | ![structure] | R¹ | ![structure] |
|---|---|---|---|
| —C₂H₅ | 2-methyl-4-(SC₂H₅)-6-(NHCH₃)-1,3,5-triazine | —C₂H₅ | 2-methyl-4-(SC₂H₅)-6-N(CH₃)₂-1,3,5-triazine |
| —C₂H₅ | 2-methyl-4-(SC₂H₅)-6-N(C₂H₅)₂-1,3,5-triazine | —C₂H₅ | 4,5-dimethyl-pyridazine |
| —C₂H₅ | 2-methyl-4,6-bis(SCH₃)-1,3,5-triazine | —C₂H₅ | 2-methyl-4,6-bis(SC₂H₅)-1,3,5-triazine |
| —CH₃ | 2-methyl-4-CF₃-6-OCH₃-pyrimidine | —CH₂-C₆H₅ | 2-methyl-4-OCH₃-6-Cl-pyrimidine |
| —CH₃ | 2-methyl-4-CF₃-6-CH₃-pyrimidine | —CH₂-C₆H₅ | 2-methyl-4-Cl-6-CH₃-pyrimidine |
| —CH₃ | 2-methyl-4-C₂H₅-6-OCH₃-pyrimidine | —CH₂-C₆H₅ | 2-methyl-4-Cl-6-OCH₃-pyrimidine |
| —C₃H₇-n | 2,4,6-trimethyl-pyrimidine | —C₃H₇-n | 2,4-dimethyl-pyrimidine |

TABLE 1-continued $$R^1-NH-\underset{X}{\overset{N-Z}{\underset{\parallel}{\bigg|}}}\underset{R^2}{\overset{Y}{\bigg|}} \quad (III)$$

| R$^1$ | ring | R$^1$ | ring |
|---|---|---|---|
| —C$_3$H$_7$-n | 4-CH$_3$, 6-OCH$_3$ pyrimidine | —C$_3$H$_7$-n | 4-C$_2$H$_5$ pyrimidine |
| —C$_3$H$_7$-n | 4-OCH$_3$, 6-OCH$_3$ pyrimidine | —C$_3$H$_7$-n | 4-OCHF$_2$, 6-CH$_3$ pyrimidine |
| —C$_3$H$_7$-n | 4-OC$_2$H$_5$, 6-OC$_2$H$_5$ pyrimidine | —C$_3$H$_7$-n | 4-OCH$_3$, 6-OCH$_3$ triazine |
| —C$_3$H$_7$-n | 4-CH$_3$, 6-CH$_3$ triazine | —C$_3$H$_7$-n | 4-CH$_3$, 6-SCH$_3$ triazine |
| —C$_3$H$_7$-n | 4-OCH$_3$, 6-CH$_3$ triazine | —C$_3$H$_7$-n | 4-OC$_2$H$_5$, 6-CH$_3$ triazine |
| —C$_3$H$_7$-n | 4-OC$_2$H$_5$, 6-OC$_2$H$_5$ triazine | —C$_3$H$_7$-n | 4-OC$_2$H$_5$, 6-OCH$_3$ triazine |
| —CH$_2$—CH=CH$_2$ | 4-CH$_3$, 6-CH$_3$ pyrimidine | —CH$_2$—CH=CH$_2$ | 4-CH$_3$ pyrimidine |

TABLE 1-continued $$R^1-NH-\overset{N-Z}{\underset{X}{\bigvee}}\overset{Y}{\underset{R^2}{\bigvee}} \quad (III)$$

| R¹ | structure | R¹ | structure |
|---|---|---|---|
| —CH₂—CH=CH₂ | 4-CH₃, 6-OCH₃ pyrimidine | —CH₂—CH=CH₂ | 4-C₂H₅ pyrimidine |
| —CH₂—CH=CH₂ | 4-OCH₃, 6-OCH₃ pyrimidine | —CH₂—CH=CH₂ | 4-OCHF₂, 6-CH₃ pyrimidine |
| —CH₂—CH=CH₂ | 4-CH₃, 6-CH₃ triazine | —CH₂—CH=CH₂ | 4-OCH₃, 6-OCH₃ triazine |
| —CH₂—CH=CH₂ | 4-OCH₃, 6-CH₃ triazine | —CH₂—CH=CH₂ | 4-OC₂H₅, 6-CH₃ triazine |
| —CH₂—CH=CH₂ | 4-OC₂H₅, 6-OC₂H₅ triazine | —CH₂—CH=CH₂ | 4-OC₂H₅, 6-OCH₃ triazine |
| —CH₂—CH=CH₂ | 4-CH₃, 6-SCH₃ triazine | H | 4-OCHF₂, 6-OCHF₂ pyrimidine |
| H | 4-C₂H₅, 6-OCH₃ pyrimidine | H | 4-OCHF₂, 6-CF₃ pyrimidine |

TABLE 1-continued

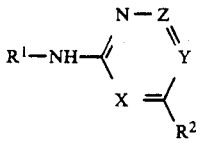

| R¹ | (structure) | R¹ | (structure) |
|---|---|---|---|
| H | 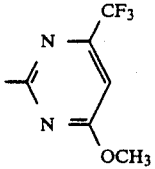 | H | 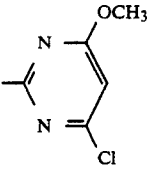 |
| H | 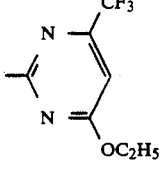 | H | 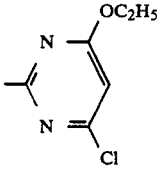 |
| H | 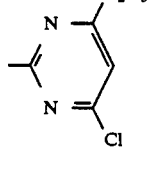 | H | 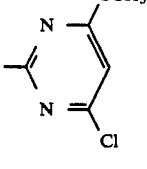 |
| H | 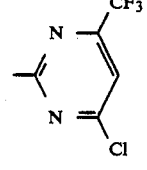 | H | 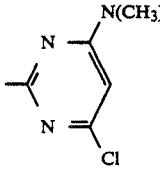 |
| H | 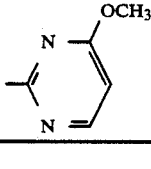 | | |

The compounds of the formula (III) are known and can be prepared by processes which are known per se (compare, for example, Chem. Pharm. Bull. 11 (1963), 1382 and U.S. Pat. No. 4,299,960, European Patent No. A-121,082, European Patent No. A-125,205, European Patent No. A-126,711 and European Patent No. A-152,378).

The process according to the invention for the preparation of the new compounds of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylene sulphone and hexamethylphosphoric acid triamide.

If appropriate, the process according to the invention is carried out in the presence of a catalyst. Catalysts include, in particular, aliphatic, aromatic or heterocyclic amines, such as triethylamine, N,N-dimethylaniline, pyridine, 2-methyl-5-ethyl-pyridine, 4-dimethyl-aminopyridine, diazabicyclooctane (DABCO), diazabicyclononene (DBN) and diazabicycloundecene (DBU).

The reaction temperatures can be varied within a substantial range in the process according to the invention. The reaction is in general carried out at temperatures between 0° C. and 150° C., preferably at temperatures between 206° C. and 100° C.

The process according to the invention is in general carried out under normal pressure. However, it is also possible for the process to be carried out under increased or reduced pressure.

For carrying out the process according to the invention, in general 1.0 to 3.0 mols preferably 1.0 to 2.0 mols of 2-halogenoalkoxy-benzenesulphonyl iso(thio)cyanate of the formula (II) are employed per mol of hetereoarylamine of the formula (III).

The starting substances of the formulae (II) and (III) and if appropriate the catalyst and the diluent are in general brought together at room temperature or with gentle external cooling and the reaction mixture is stirred, if appropriate at elevated temperature, until the reaction has ended.

The new compounds of the formula (I) are worked up and isolated by customary methods: if the compounds of the formula (I) are obtained as crystals, they are isolated by filtration with suction. Otherwise—if appropriate after concentration—water and an organic solvent which is virtually water-immiscible are added and, after thorough shaking, the organic phase is separated off, dried, filtered and concentrated, the products of the formula (I) remaining in the residue.

The active compounds according to the invention can be used as defoliants, desiccants, agents for destroying broad-leaved plants and, especially, as weedkillers. By weeds, in the broadest sense, there are to be understood all plants which grow in locations where they are undesired Whether the substances according to the invention act as total or selective herbicides depends essentially on the amount used.

The active compounds according to the invention can be used, for example, in connection with the following plants:

Dicotyledon- weeds of the genera: Sinapis, Lepidium, Galium, Stellaria, Matricaria, Anthemis, Galinsoga, Cheno-podium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The new active compounds of the formula (I) are suitable for selectively combating dicotyledon weeds in monocotyledon crops by the pre-emergence and post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as poly-oxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl) N,N'-dimethylurea, 3-(3-chloro-4-methylphenyl)-1,1-dimethylurea, 3-(4-isopropylphenyl)-1,1-dimethylurea, 1-(4-methyl-phenyl)-3-(1-methyl-1-phenyl-ethyl)-urea, 2-chloro-N-{[4-methoxy-6-methyl-1,3,5-triazin-2-yl)-amino]carbonyl}-benzenesulphonamide, ethyl 2-{[(4-chloro-6-methoxy-2-pyrimidyl)aminocarbonyl-]aminosulphonyl}benzoate, 2-ethylamino-6-(1,1-dimethylethyl-amino)-4-methylthio-1,3,5-triazine, 2-chloro-4-ethylamino-6-(1-methyl-ethyl)-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, 5-(2-chloro-4-trifluoromethyl-phenoxy)-N-methylsulphonyl-2-nitrobenzamide, 2-ethoxy-1-methyl-2-oxo-ethyl 5-(2-chloro-4-trifluoromethyl-phenoxy)-2-nitrobenzoate, methyl 2-[4-(2,4-dichlorophenoxy)-phenoxy}-propionate, 2-{4-[(3-chloro-5-trifluoromethyl-2-pyridinyl)oxy]-phenoxy}-propionic acid, the R-enantiomer of (trimethylsilyl)-methyl 2-{4-[(3,5-dichloro-2-pyridinyl)oxy]-phenoxy}-propionate, 2,4-dichlorophenoxyacetic acid, 2-(2,4-dichlorophenoxy)-propionic acid, 4-chloro-2-methyl-phenoxy-acetic acid, 2-(4-chloro-2-methyl phenoxy)-propionic acid, 3,5-diiodo-4-hydroxy-benzonitrile, 3,5-dibromo-4-hydroxy-benzonitrile, 2-[5-methyl-5-(1-methylethyl)-4-oxo-2-imidazolin-2-yl]-3-pyridine carboxylic acid, 2-(1-ethoxyamino-butylidene)-5-(2-ethylthiopropyl)-1,3-cyclohexaned-ione, [(4-amino-3,5-dichloro-6-fluoro-2-pyridyl)oxy]-acetic acid, 3-isopropyl-2,1,3-benzothiadiazin-4-one 2,2-dioxide, 2-(2-benzothiazolyloxy)-N-methyl-N-phenyl-acetamide, S-ethyl N,N-dipropylthiocarbamate, 1-ethylthiocarbonyl-hexahydro-1H-azepine, propionic acid 3,4-dichloroanilide, chloroacetic acid N-(2,6-diethyl-phenyl)-N-methoxymethyl-amide, chloroacetic acid N-(2-ethyl-6-methyl-phenyl)-N-(2-methoxy-1-methyle-thyl)-amide, chloroacetic acid N-(2,6-dimethyl-phenyl)-N-(1H-pyrazol-1-yl-methyl)-amide, chloroacetic acid N-(2,6-diethylphenyl)-N-(2-propoxyethyl)-amide, 3,7-dichloro-8-quinolinecarboxylic acid, 4-(2,4-dichloro-phenoxy)-2-methoxy-aniline, ethyl 2-(-((6-chloro-ben-zoxazol-2-yl)-oxy)-phenoxy)-propionate, (2,4-dichloro-phenyl)-(1,3-dimethyl-5-((4-methyl-phenyl)-sulphonyl-oxy)-1H-pyrazol-4-yl)-methanone and O-(6-chloro-3-phenyl-4-pyridazinyl) S-octyl thiocarbonate. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 5 kg of active compound per hectare of soil surface, preferably between 0.01 and 1 kg per ha.

The preparation and use of the active compounds according to the invention can be seen from the following examples.

PREPARATION EXAMPLES

EXAMPLE 1

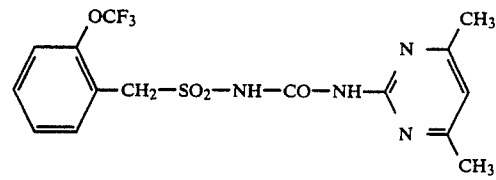

A solution of 2-trifluoromethoxy-benzylsulphonyl isocyanate in 100 ml of methylene chloride (for the preparation compare Example (II-1); the amount of substance obtained according to Example (II-1) is used here) is stirred with 2.5 g (0.02 mol) of 2-amino-4,6-dimethylpyrimidine at 20° C. for 12 hours The mixture is then concentrated, the residue is digested with diethyl ether and the reaction product obtained as crystals is isolated by filtration with suction.

6.0 g (74% of theory) of 1-(2-trifluoromethoxy-benzylsulphonyl)-3-(4,6-dimethyl-pyrimidin-2-yl)-urea of melting point 151° C. (decomposition) are obtained.

The compounds of the formula (I) shown in Table 2 below can be prepared by the process described by way of example in Example 1:

TABLE 2

Structure (I):

Ar-CH(R³)-SO₂-NH-C(=Q)-N(R¹)-C(=NZ)(X=CR²-Y) where Ar = 2-OR⁴-phenyl

| Example No. | R¹ | R³ | R⁴ | Q | Substituent group | Melting point (°C.) |
|---|---|---|---|---|---|---|
| 2 | H | H | CF₃ | O | pyrimidine with 4-OCH₃, 6-OCH₃ | 170 (decomp.) |
| 3 | H | H | CF₃ | O | pyrimidine with 4-OCH₃, 6-Cl | 178 (decomp.) |
| 4 | H | H | CF₃ | O | pyrimidine with 4-CH₃, 6-OCHF₂ | 154 (decomp.) |
| 5 | H | H | CF₃ | O | pyrimidine with 4-OCHF₂, 6-OCHF₂ | 158 |
| 6 | H | H | CF₃ | O | triazine with CH₃, CH₃ | 141 (decomp.) |
| 7 | CH₃ | H | CF₃ | O | pyrimidine with 4-OCH₃, 6-OCH₃ | 98 (decomp.) |
| 8 | H | H | CF₃ | O | pyrimidine with 4-CH₃, 6-OCH₃ | 164 |

TABLE 2-continued $$\text{(I)}$$

Structure (I): 2-(OR⁴)-phenyl-CH(R³)-SO₂-NH-C(=Q)-N(R¹)-[heterocycle with N=Z, Y, X, R²]

| Example No. | R¹ | R³ | R⁴ | Q | R² (heterocycle) | Melting point (°C.) |
|---|---|---|---|---|---|---|
| 9 | CH₃ | H | CF₃ | O | 2-CH₃, 4-CH₃, 6-OCH₃ pyrimidine | |
| 10 | CH₃ | H | CF₃ | O | 2-CH₃, 4-OCH₃, 6-Cl pyrimidine | |
| 11 | H | H | CF₃ | O | 2-CH₃, 4-OC₂H₅, 6-OC₂H₅ pyrimidine | 156 |
| 12 | H | H | CF₃ | O | 2-CH₃, 4-OC₂H₅, 6-Cl pyrimidine | 170 |
| 13 | H | H | CF₃ | O | 2-CH₃, 4-C₂H₅, 6-OCH₃ pyrimidine | |
| 14 | H | H | CF₃ | O | 2-CH₃, 4-CH₃, 6-OC₂H₅ pyrimidine | |
| 15 | H | | CF₃ | O | 2-CH₃, 4-CH₃, 6-CH₃ pyrimidine | |

TABLE 2-continued $$\text{(I)}$$

| Example No. | $R^1$ | $R^3$ | $R^4$ | Q | $R^2$ ring | Melting point (°C.) |
|---|---|---|---|---|---|---|
| 16 | H | H | $CF_3$ | O | 2-methyl-4-methyl-6-chloro pyrimidine ($CH_3$, Cl) | |
| 17 | H | H | $CF_3$ | O | 2-methyl-4-ethyl-6-chloro pyrimidine ($C_2H_5$, Cl) | |
| 18 | H | H | $CF_3$ | O | 2-methyl-4-$CF_3$-6-chloro pyrimidine ($CF_3$, Cl) | |
| 19 | H | H | $CF_3$ | O | 2-methyl-4-$CF_3$-6-methoxy pyrimidine ($CF_3$, $OCH_3$) | |
| 20 | H | H | $CHF_2$ | O | 2-methyl-4,6-dimethyl pyrimidine ($CH_3$, $CH_3$) | |
| 21 | H | H | $CHF_2$ | O | 2-methyl-4,6-dimethoxy pyrimidine ($OCH_3$, $OCH_3$) | |
| 22 | $CH_3$ | H | $CHF_2$ | O | 2-methyl-4,6-dimethoxy pyrimidine ($OCH_3$, $OCH_3$) | |

TABLE 2-continued
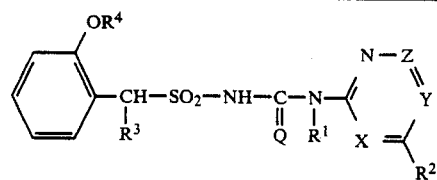
| Example No. | $R^1$ | $R^3$ | $R^4$ | Q | $R^2$ substituent | Melting point (°C.) |
|---|---|---|---|---|---|---|
| 23 | H | H | $CHF_2$ | O | 4-OCH₃, 6-Cl, 2-CH₃ pyrimidine | |
| 24 | H | H | $CHF_2$ | O | 4-OC₂H₅, 6-Cl, 2-CH₃ pyrimidine | |
| 25 | H | $CH_3$ | $CF_3$ | O | 4-OCH₃, 6-OCH₃, 2-CH₃ pyrimidine | |
| 26 | H | H | $CHF_2$ | O | 4-OC₂H₅, 6-OC₂H₅, 2-CH₃ pyrimidine | |
| 27 | H | H | $CF_3$ | O | 4-CH₃, 6-CH₃ triazine | |
| 28 | H | H | $CF_3$ | O | 4-OCH₃, 6-CH₃ triazine | |
| 29 | $CH_3$ | H | $CF_3$ | O | 4-OCH₃, 6-CH₃ triazine | |

TABLE 2-continued (I) Structure: 2-(OR⁴)-C₆H₄-CH(R³)-SO₂-NH-C(=Q)-N(R¹)-[heterocycle with N=Z, Y, X, R²]

| Example No. | R¹ | R³ | R⁴ | Q | R² (heterocycle) | Melting point (°C.) |
|---|---|---|---|---|---|---|
| 30 | H | CH₃ | CF₃ | O | triazine: 4-OCH₃, 6-CH₃ | |
| 31 | H | H | CF₃ | O | triazine: 4-OCH₃, 6-OCH₃ | |
| 32 | CH₃ | H | CF₃ | O | triazine: 4-OCH₃, 6-OCH₃ | |
| 33 | H | H | CHF₂ | O | triazine: 4-OCH₃, 6-OCH₃ | |
| 34 | H | H | CClF₂ | O | pyrimidine: 4-OCH₃, 6-OCH₃ | |
| 35 | H | H | CFCl₂ | O | pyrimidine: 4-OCH₃, 6-OCH₃ | |
| 36 | H | H | CH₂CH₂Cl | O | pyrimidine: 4-OCH₃, 6-OCH₃ | |

TABLE 2-continued $$\text{(I)}$$

Structure: 2-(OR⁴)-C₆H₄-CH(R³)-SO₂-NH-C(Q)-N(R¹)-[heterocycle with N=Z, X, Y, R²]

| Example No. | R¹ | R³ | R⁴ | Q | [heterocycle substituent] | Melting point (°C.) |
|---|---|---|---|---|---|---|
| 37 | H | H | CH₂CH₂Cl | O | 4-CH₃, 6-OCH₃ pyrimidine | |
| 38 | H | H | CH₂CH₂Cl | O | 4,6-di-OCH₃ triazine | |
| 39 | H | H | CF₂CHF₂ | O | 4,6-di-OCH₃ pyrimidine | |
| 40 | H | H | CF₂CHF₂ | O | 4-CH₃, 6-OCH₃ triazine | |
| 41 | H | H | CF₂CHFCl | O | 4,6-di-OCH₃ pyrimidine | |
| 42 | H | H | CF₂CHFCl | O | 4-CH₃, 6-OCH₃ triazine | |
| 43 | H | H | CF₃ | O | 4-CH₃ pyrimidine | 193 |

TABLE 2-continued $$\text{(I)}$$

Structure (I): 2-(OR⁴)-phenyl-CH(R³)-SO₂-NH-C(Q)-N(R¹)-[heterocycle with N=Z, X, Y, R²]

| Example No. | R¹ | R³ | R⁴ | Q | R² (heterocycle) | Melting point (°C.) |
|---|---|---|---|---|---|---|
| 44 | H | H | CF₃ | O | pyrimidine: 4-OCH₃ | 106 |
| 45 | H | H | CF₃ | O | pyrimidine: 4-C₂H₅ | |
| 46 | H | H | CF₃ | O | pyrimidine: 4-OCHF₂, 6-CF₃ | 132 |
| 47 | H | H | CF₃ | O | pyrimidine: 4-OC₂H₅, 6-OCH₃ | |
| 48 | H | H | CF₃ | O | pyrimidine: 4-OC₂H₅, 6-C₂H₅ | |
| 49 | H | H | CF₃ | O | pyrimidine: 4-N(CH₃)₂, 6-Cl | |
| 50 | H | H | CHF₂ | O | pyrimidine: 4-OCH₃ | |

TABLE 2-continued (I) Structure: 2-(OR⁴)-C₆H₄-CH(R³)-SO₂-NH-C(Q)-N(R¹)-C(=N-Z...)...

| Example No. | R¹ | R³ | R⁴ | Q | R² substituent (heterocycle) | Melting point (°C.) |
|---|---|---|---|---|---|---|
| 51 | H | H | CHF₂ | O | pyrimidine: 4-OCH₃, 6-CH₃ | |
| 52 | H | H | CHF₂ | O | pyrimidine: 4-OCHF₂, 6-CH₃ | |
| 53 | H | H | CHF₂ | O | pyrimidine: 4-OCH₃, 6-CF₃ | |
| 54 | H | H | CHF₂ | O | pyrimidine: 4-OCHF₂, 6-CF₃ | |
| 55 | H | H | CHF₂ | O | pyrimidine: 4-OCHF₂, 6-OCHF₂ | |
| 56 | H | H | CHF₂ | O | pyrimidine: 4-CH₃, 6-Cl | |
| 57 | H | H | CHF₂ | O | pyrimidine: 4-CF₃, 6-Cl | |

TABLE 2-continued
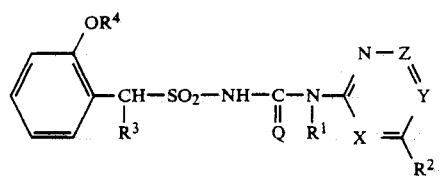
| Example No. | $R^1$ | $R^3$ | $R^4$ | Q | $R^2$ | Melting point (°C.) |
|---|---|---|---|---|---|---|
| 58 | H | H | $CHF_2$ | O | (pyrimidine: 4-$C_2H_5$, 2-CH at ring, 6-Cl) | |
| 59 | H | H | $CHF_2$ | O | (pyrimidine: 4-$OCH_3$, 6-$C_2H_5$) | |
| 60 | H | H | $CHF_2$ | O | (pyrimidine: 4-$CH_3$) | |
| 61 | H | H | $CHF_2$ | O | (pyrimidine: 4-$C_2H_5$) | |
| 62 | H | H | $CHF_2$ | O | (triazine: $CH_3$, $CH_3$) | |
| 63 | H | H | $CHF_2$ | O | (pyrimidine: 4-$OC_2H_5$, 6-$OCH_3$) | |
| 64 | H | H | $CHF_2$ | O | (pyrimidine: 4-$OC_2H_5$, 6-$CH_3$) | |

TABLE 2-continued (I) Structure: 2-(OR⁴)-C₆H₄-CH(R³)-SO₂-NH-C(=Q)-N(R¹)-C(X=...)(=N-Z-Y=C(R²)-)

| Example No. | R¹ | R³ | R⁴ | Q | R² (heterocycle) | Melting point (°C.) |
|---|---|---|---|---|---|---|
| 65 | H | H | CHF₂ | O | pyrimidine with OC₂H₅ and C₂H₅ | |
| 66 | H | H | CHF₂ | O | pyrimidine with N(CH₃)₂ and Cl | |
| 67 | H | H | CHF₂ | O | triazine with CH₃ and CH₃ | |
| 68 | CH₃ | H | CHF₂ | O | triazine with CH₃ and CH₃ | |
| 69 | CH₃ | H | CF₃ | O | triazine with CH₃ and CH₃ | |
| 70 | CH₃ | H | CHF₂ | O | triazine with OCH₃ and CH₃ | |
| 71 | H | H | CHF₂ | O | triazine with OCH₃ and CH₃ | |

TABLE 2-continued
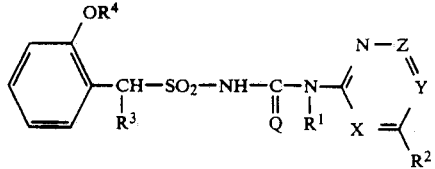
(I)
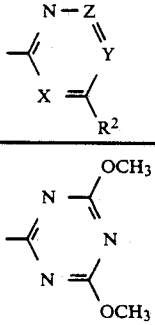
| Example No. | R¹ | R³ | R⁴ | Q | $\underset{X \underset{R^2}{\underset{\parallel}{\overset{N-Z}{\diagup}}}}{}$ | Melting point (°C.) |
|---|---|---|---|---|---|---|
| 72 | CH₃ | H | CHF₂ | O | 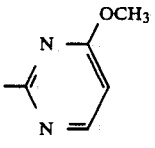 | |
| 73 | CH₃ | H | CF₃ | O | 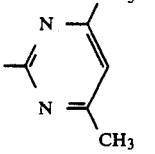 | |
| 74 | CH₃ | H | CHF₂ | O | | |
| 75 | H | H | CH₂CH₂Cl | O | | |
| 76 | H | H | CH₂CH₂Cl | O | 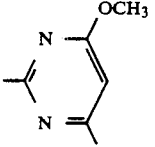 | |
| 77 | H | H | CH₂CH₂Cl | O | 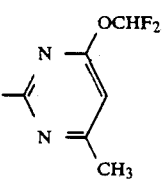 | |
| 78 | H | H | CH₂CH₂Cl | O | 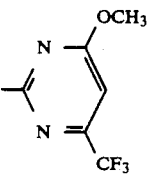 | |

TABLE 2-continued (I)

Structure: Ar(OR⁴)-CH(R³)-SO₂-NH-C(=Q)-N(R¹)-[heterocycle with N=Z, X, Y, R²]

| Example No. | R¹ | R³ | R⁴ | Q | [N=Z / X=Y / R²] | Melting point (°C.) |
|---|---|---|---|---|---|---|
| 79 | H | H | CH₂CH₂Cl | O | pyrimidine: OCH₃, Cl | |
| 80 | H | H | CH₂CH₂Cl | O | pyrimidine: OCHF₂, CF₃ | |
| 81 | H | H | CH₂CH₂Cl | O | pyrimidine: N(CH₃)₂, Cl | |
| 82 | H | H | CH₂CH₂Cl | O | triazine: CH₃, CH₃ | |
| 83 | H | H | CH₂CH₂Cl | O | pyrimidine: OCH₃, H | |
| 84 | CH₃ | H | CH₂CH₂Cl | O | triazine: CH₃, CH₃ | |
| 85 | CH₃ | H | CH₂CH₂Cl | O | triazine: OCH₃, CH₃ | |

TABLE 2-continued $$\text{(I)}$$

Structure (I): 2-(OR⁴)-phenyl-CH(R³)-SO₂-NH-C(Q)-N(R¹)-C(=N-Z...Y...X=C(R²))

| Example No. | R¹ | R³ | R⁴ | Q | R² heterocycle | Melting point (°C.) |
|---|---|---|---|---|---|---|
| 86 | CH₃ | H | CH₂CH₂Cl | O | 4,6-dimethoxy-1,3,5-triazin-2-yl | |
| 87 | H | H | CH₂—CF₃ | O | 4,6-dimethoxypyrimidin-2-yl | |
| 88 | CH₃ | H | CH₂—CF₃ | O | 4,6-dimethoxypyrimidin-2-yl | |
| 89 | H | H | CH₂—CF₃ | O | 4-methoxy-6-chloropyrimidin-2-yl | |
| 90 | H | H | CH₂—CF₃ | O | 4-methoxy-6-methylpyrimidin-2-yl | |
| 91 | H | H | CH₂—CF₃ | O | 4,6-dimethylpyrimidin-2-yl | |
| 92 | H | H | CH₂—CF₃ | S | 4,6-dimethoxypyrimidin-2-yl | |

TABLE 2-continued (I)

Structure: Ar(OR⁴)-CH(R³)-SO₂-NH-C(Q)-N(R¹)-[heterocycle with N=Z, X, Y, R²]

Heterocycle: 6-membered ring with N-Z, Y, X=, R²

| Example No. | R¹ | R³ | R⁴ | Q | R² | Melting point (°C.) |
|---|---|---|---|---|---|---|
| 93 | H | H | CH₂CH₂Cl | S | 4,6-dimethoxypyrimidin-2-yl | |
| 94 | CH₃ | H | CH₂CH₂Cl | S | 4,6-dimethoxypyrimidin-2-yl | |
| 95 | H | H | CHF₂ | S | 4,6-dimethoxypyrimidin-2-yl | |
| 96 | CH₃ | H | CHF₂ | S | 4,6-dimethoxypyrimidin-2-yl | |
| 97 | H | H | CF₃ | S | 4,6-dimethoxypyrimidin-2-yl | |
| 98 | CH₃ | H | CF₃ | S | 4,6-dimethoxypyrimidin-2-yl | |
| 99 | H | H | CF₃ | S | 4-methoxy-6-methyl-1,3,5-triazin-2-yl | |

TABLE 2-continued

Structure (I): 2-(OR⁴)-C₆H₄-CH(R³)-SO₂-NH-C(=Q)-N(R¹)-C(=X-C(R²)=Y-N=Z-N) (pyrimidine/triazine ring)

| Example No. | R¹ | R³ | R⁴ | Q | R² (ring substituent) | Melting point (°C.) |
|---|---|---|---|---|---|---|
| 100 | CH₃ | H | CF₃ | S | triazine: OCH₃ / CH₃ | |
| 101 | H | H | CHF₂ | S | triazine: OCH₃ / CH₃ | |
| 102 | CH₃ | H | CHF₂ | S | triazine: OCH₃ / CH₃ | |
| 103 | H | H | CH₂CH₂Cl | S | triazine: OCH₃ / CH₃ | |
| 104 | CH₃ | H | CH₂CH₂Cl | S | triazine: OCH₃ / CH₃ | |
| 105 | H | H | CF₃ | O | triazine: NHCH₃ / CH₃ | |
| 106 | H | H | CF₃ | O | triazine: NHCH₃ / OCH₃ | |

TABLE 2-continued $$\text{(I)}$$

Structure: 2-(OR⁴)-C₆H₄-CH(R³)-SO₂-NH-C(Q)-N(R¹)-C(=N-Z...)-X=C(R²)-Y (sulfonylurea with heterocycle)

| Example No. | R¹ | R³ | R⁴ | Q | (N=Z, X, Y, R²) heterocycle | Melting point (°C.) |
|---|---|---|---|---|---|---|
| 107 | CH₃ | H | CF₃ | O | Triazine with NHCH₃ and CH₃ substituents | |
| 108 | CH₃ | H | CF₃ | O | Triazine with NHCH₃ and OCH₃ substituents | |
| 109 | H | H | CF₃ | O | Triazine with OC₂H₅ and CH₃ substituents | |
| 110 | H | H | CHF₂ | O | Triazine with OC₂H₅ and CH₃ substituents | |
| 111 | CH₃ | H | CF₃ | O | Triazine with OC₂H₅ and CH₃ substituents | |
| 112 | CH₃ | H | CHF₂ | O | Triazine with OC₂H₅ and CH₃ substituents | |
| 113 | H | H | CF₃ | O | Triazine with OC₂H₅ and NHCH₃ substituents | |

TABLE 2-continued

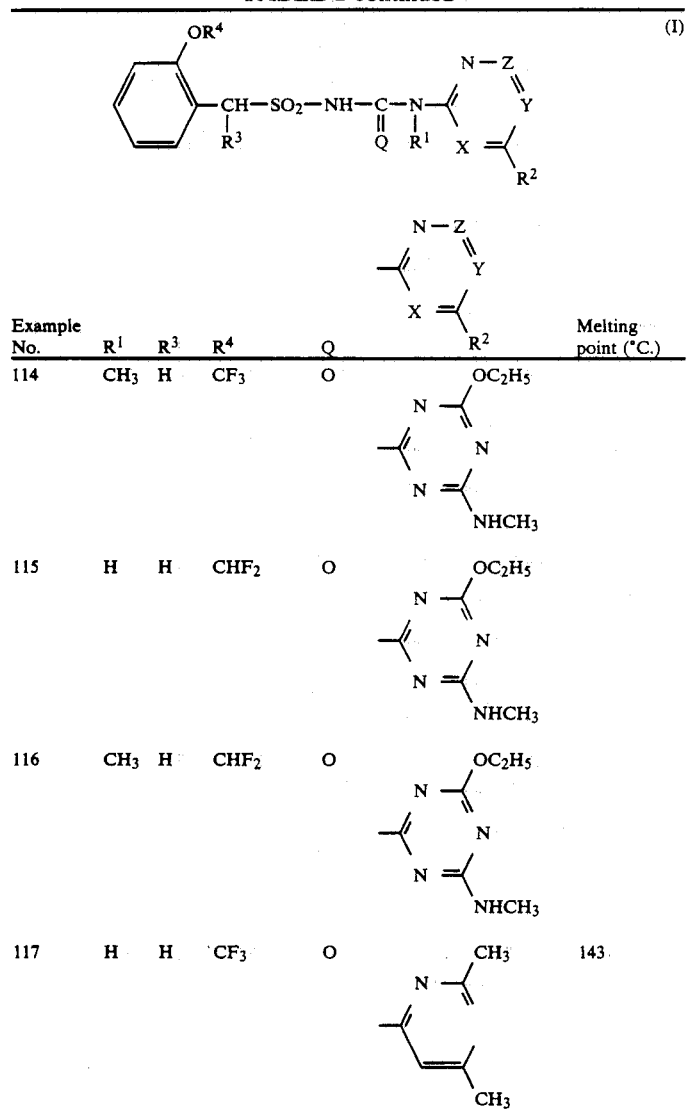

| Example No. | R¹ | R³ | R⁴ | Q | R² | Melting point (°C.) |
|---|---|---|---|---|---|---|
| 114 | CH₃ | H | CF₃ | O | (pyrimidine with OC₂H₅ and NHCH₃, triazine ring) | |
| 115 | H | H | CHF₂ | O | (pyrimidine with OC₂H₅ and NHCH₃, triazine ring) | |
| 116 | CH₃ | H | CHF₂ | O | (pyrimidine with OC₂H₅ and NHCH₃, triazine ring) | |
| 117 | H | H | CF₃ | O | (pyrimidine with two CH₃ groups) | 143 |

Starting substances of the formula (II)

EXAMPLE (II-1)

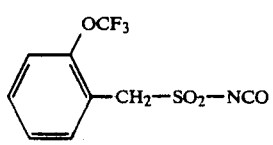

A mixture of 8.9 g (0.035 mol) of 2-trifluoromethoxy-benzylsulphonic acid amide, 3.5 g (0.035 mol) of n-butyl isocyanate, 0.2 g of diaza-bicyclo-[2,2,2]-octane (DABCO) and 150 ml of anhydrous xylene is heated to the reflux temperature and a weak stream of phosgene is passed through for two hours. The mixture is subsequently stirred under reflux for a further 30 minutes and is then cooled, filtered and concentrated. The residue is taken up in methylene chloride and filtered again. The filtrate contains 2-trifluoromethoxy-benzylsulphonyl isocyanate as crude material mixed with DABCO and is further used as such for the subsequent reaction, since partial decomposition occurs on distillation under a high vacuum The compounds of the formula (II) listed in Table 3 below can be prepared by the process described by way of example in Example (II-1):

TABLE 3

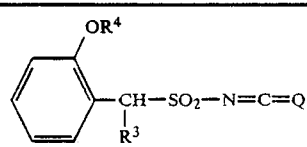

| Example No. | R³ | R⁴ | Q | Physical constants |
|---|---|---|---|---|
| (II-2) | H | CHF₂ | O | |
| (II-3) | H | CF₂CHF₂ | O | |
| (II-4) | H | CF₂CHFCl | O | |
| (II-5) | CH₃ | CF₃ | O | |
| (II-6) | CH₃ | CHF₂ | O | |
| (II-7) | H | CH₂—CF₃ | O | |
| (II-8) | H | CH₂CH₂Cl | O | |
| (II-9) | CH₃ | CH₂—CF₃ | O | |
| (II-10) | CH₃ | CH₂CH₂Cl | O | |
| (II-11) | H | CClF₂ | O | |

TABLE 3-continued

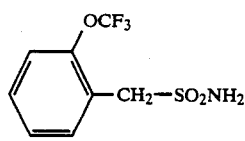

(II)

| Example No. | $R^3$ | $R^4$ | Q | Physical constants |
|---|---|---|---|---|
| (II-12) | H | CCl$_2$F | O | |

Intermediate products of the formula (IV)

EXAMPLE (IV-1)

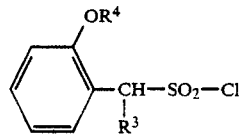

205.9 g (0.75 mol) of 2-trifluoromethoxy-benzylsulfonyl chloride are introduced into 1.5 l of saturated aqueous ammonia solution at 30° C.–40° C. and the mixture is subsequently stirred at 50° C.–60° C. for 3 hours. After cooling, the precipitate which has separated out is filtered off with suction, washed neutral with water and dried.

136.5 g (71% of theory) of 2-trifluoromethoxybenzylsulphonic acid amide of melting point 127° C. are obtained.

The compounds of the formula (IV) listed in Table 4 below can be prepared by the process described by way of example in Example (IV-1):

TABLE 4

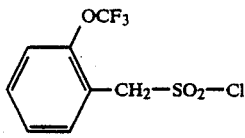

(IV)

| Example No. | $R^3$ | $R^4$ | Melting point [°C.] |
|---|---|---|---|
| (IV-2) | H | CHF$_2$ | |
| (IV-3) | H | CF$_2$CHF$_2$ | |
| (IV-4) | H | CF$_2$CHFCl | |
| (IV-5) | CH$_3$ | CF$_3$ | |
| (IV-6) | CH$_3$ | CHF$_2$ | |
| (IV-7) | H | CH$_2$—CF$_3$ | |
| (IV-8) | H | CH$_2$CH$_2$Cl | |
| (IV-9) | CH$_3$ | CH$_2$—CF$_3$ | |
| (IV-10) | CH$_3$ | CH$_2$CH$_2$Cl | |
| (IV-11) | H | CClF$_2$ | |
| (IV-12) | H | CCl$_2$F | |

Intermediate products of the formula (IX)

EXAMPLE (IX-1)

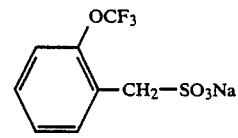

23.7 g (0.085 mol) of sodium 2-trifluoromethoxybenzylsulphonate are mixed with 35.5 g (0.17 mol) of phosphorus pentachloride and the mixture is rotated on a rotary evaporator at a bath temperature of 80° C.–90° C. for about 2 hours. It is cooled and the phosphorus oxychloride formed is removed in vacuo. The residue is suspended in methylene chloride and poured onto icewater. The organic phase is separated off, washed neutral, dried and concentrated.

19.0 g (81.4% of theory) of 2-trifluoromethoxybenzylsulphonyl chloride are obtained as crude material which is sufficiently pure for the following reaction to give the sulphonamide. For purification, the crude material can be taken up in methylene chloride and purified over silica gel: $n_D^{22.5} = 1.4854$.

The compounds of the formula (IX) listed in Table 5 below can be prepared by the process described by way of example in Example (IX-1):

TABLE 5

(IX)

| Example No. | $R^3$ | $R^4$ | Physical constants |
|---|---|---|---|
| (IX-2) | H | CHF$_2$ | |
| (IX-3) | H | CF$_2$CHF$_2$ | |
| (IX-4) | H | CF$_2$CHFCl | |
| (IX-5) | CH$_3$ | CF$_3$ | |
| (IX-6) | CH$_3$ | CHF$_2$ | |
| (IX-7) | H | CH$_2$—CF$_3$ | |
| (IX-8) | H | CH$_2$CH$_2$Cl | |
| (IX-9) | CH$_3$ | CH$_2$—CF$_3$ | |
| (IX-10) | CH$_3$ | CH$_2$CH$_2$Cl | |
| (IX-11) | H | CClF$_2$ | |
| (IX-12) | H | CCl$_2$F | |

Intermediate products of the formula (X)

EXAMPLE (X-1)

21.0 g (0.1 mol) of 2-trifluoromethoxybenzyl chloride are heated under reflux with a saturated solution of 13.9 g (0.11 mol) of sodium thiosulphate in water for 5 hours, with thorough stirring. After cooling, the white precipitate which has separated out is filtered off with suction and rinsed with a little ice-cold water.

After drying over phosphorus pentoxide, 26.4 g (95% of theory) of sodium 2-trifluoromethoxy-benzylsulphonate of melting point 115° C. are obtained The compounds of the formula (X) listed in Table 6 below can be prepared by the process described by way of example in Example (X-1):

TABLE 6

(X)

$$\text{OR}^4\text{-C}_6\text{H}_4\text{-CH(R}^3\text{)-SO}_3\text{M}$$

| Example No. | R³ | R⁴ | M | Melting point [°C.] |
|---|---|---|---|---|
| (X-2) | H | CHF₂ | Na | |
| (X-3) | H | CF₂CHF₂ | Na | |
| (X-4) | H | CF₂CHFCl | Na | |
| (X-5) | CH₃ | CF₃ | Na | |
| (X-6) | CH₃ | CHF₂ | Na | |
| (X-7) | H | CH₂—CF₃ | Na | |
| (X-8) | H | CH₂CH₂Cl | Na | |
| (X-9) | CH₃ | CH₂—CF₃ | Na | |
| (X-10) | CH₃ | CH₂CH₂Cl | Na | |
| (X-11) | H | CClF₂ | Na | |
| (X-12) | H | CCl₂F | Na | |
| (X-13) | H | CF₃ | K | |

Intermediate products of the formula (XI)

EXAMPLE (XI-1)

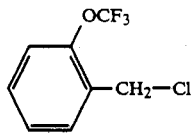

900 g (5.1 mol) of 2-trifluoromethoxy-toluene (2-methyl-trifluoroanisole) are heated to 100° C. and 180 g (2.54 mol) of chlorine are passed in at this temperature under UV irradiation. Nitrogen is then bubbled through and the reaction mixture is subjected to fractional distillation under reduced pressure.

425 g (40% of theory) of 2-trifluoromethoxy-benzyl chloride (2-chloromethyl-trifluoroanisole) of boiling point 110° C./100 mbar and refractive index $n_D^{20}=1.5450$ are obtained as the main fraction.

The compounds of the formula (XI) listed in Table 7 below can be prepared by the process described by way of example in Example (XI-1):

TABLE 7

(XI)

$$\text{OR}^4\text{-C}_6\text{H}_4\text{-CH(R}^3\text{)-Cl}$$

| Example No. | R³ | R⁴ | Refractive index |
|---|---|---|---|
| (XI-2) | H | CHF₂ | |
| (XI-3) | H | CF₂CHF₂ | |
| (XI-4) | H | CF₂CHFCl | |
| (XI-5) | CH₃ | CF₃ | |
| (XI-6) | CH₃ | CHF₂ | |
| (XI-7) | H | CH₂—CF₃ | |
| (XI-8) | H | CH₂CH₂Cl | |
| (XI-9) | CH₃ | CH₂—CF₃ | |
| (XI-10) | H | CF₂Cl | |
| (XI-11) | H | CFCl₂ | |

Use Examples

The compound shown below is employed as the comparison substance in the following use examples:

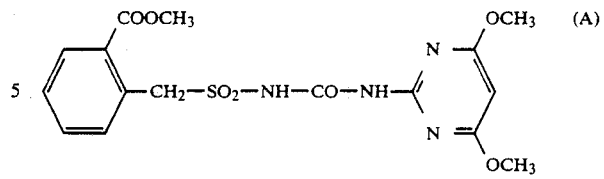

(A)

1-(2-Methoxycarbonyl-benzylsulphonyl)-3-(4,6-dimethoxypyrimidin-2-yl)-urea (known from U.S. Pat. No. 4,420,325).

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area The concentration of the active compound in the preparation is of no importance, only the amount of active compound applied per unit area being decisive. After three weeks, the degree of damage to the plants is rated in % damage in comparison to the development of the untreated control The figures denote:

0%=no action (like untreated control)

100%=total destruction

In this test, the active compounds according to the invention exhibit a very good herbicidal activity. For example, in this test, the active compound according to Preparation Example (2) exhibits a better tolerance towards crop plants, such as, for example, rice and corn , and a better action against problem weeds, such as, for example, Galium and Ipomoea, than comparison compound (A).

EXAMPLE B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:

0% =no action (like untreated control)

100% =total destruction

In this test, the active compounds according to the invention exhibit a very good herbicidal activity. For example, in this test, the active compound according to Preparation Example (2) exhibits a better tolerance towards crop plants, such as, for example, corn, and a better action against problem weeds, such as, for example, Amaranthus, Datura, Sinapis and Xanthium, than comparison compound (A).

It will be understood that the specification and examples are illustrative but not limitative of the present invention and that other embodiments within the spirit and scope of the invention will suggest themselves to those skilled in the art.

We claim:

1. A 2-halogenoalkoxybenzylsulphonyl derivative of the formula

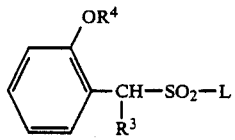

in which
R$^3$ represents hydrogen or alkyl,
R$^4$ represents halogenoalkyl,
L represents —N=C=O, —N=C=S, —NH$_2$, Cl, OH or OM, and
M represents an alkali metal.

2. A compound according to claim 1, in which L represents —N=C=O or —N=C=S.

3. A compound according to claim 1, in which L represents —NH$_2$.

4. A compound according to claim 1, in which L represents Cl.

5. A compound according to claim 1, in which L represents OH.

6. A compound according to claim 1, in which L represents OM and M represents an alkali metal.

7. 2-Trifluoromethoxy-benzyl chloride of the formula

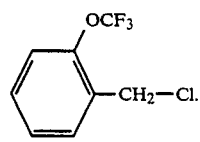

* * * * *